(12) United States Patent
Itsuji

(10) Patent No.: US 7,619,736 B2
(45) Date of Patent: Nov. 17, 2009

(54) APPARATUS AND METHOD FOR OBTAINING SAMPLE INFORMATION BY DETECTING ELECTROMAGNETIC WAVE

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 413 days.

(21) Appl. No.: 11/785,771

(22) Filed: Apr. 20, 2007

(65) Prior Publication Data

US 2007/0252992 A1 Nov. 1, 2007

(30) Foreign Application Priority Data

Apr. 28, 2006 (JP) .................. 2006-125669

(51) Int. Cl.
*G01J 4/00* (2006.01)
(52) U.S. Cl. .................. 356/370; 356/369; 250/341.3; 250/225
(58) Field of Classification Search ......... 356/364–370; 250/341.3, 225
See application file for complete search history.

(56) References Cited

U.S. PATENT DOCUMENTS

| | | | |
|---|---|---|---|
| 6,448,553 B1 | 9/2002 | Itsuji et al. | |
| 6,661,519 B2 * | 12/2003 | Fukasawa | ............ 356/432 |
| 6,835,925 B2 | 12/2004 | Itsuji et al. | |
| 6,847,448 B2 * | 1/2005 | Nagashima et al. | ......... 356/364 |
| 7,248,995 B2 | 7/2007 | Itsuji et al. | |
| 2006/0061510 A1 | 3/2006 | Itsuji et al. | |
| 2007/0030115 A1 | 2/2007 | Itsuji et al. | |
| 2007/0235718 A1 | 10/2007 | Kasai et al. | |

FOREIGN PATENT DOCUMENTS

JP 2004-191302 7/2004

OTHER PUBLICATIONS

U.S. Appl. No. 10/587,262; International Filing Date: Mar. 22, 2006, Applicant: Takeaki Itsuji.

* cited by examiner

*Primary Examiner*—L. G Lauchman
(74) *Attorney, Agent, or Firm*—Fitzpatrick, Cella, Harper & Scinto

(57) ABSTRACT

A sample information obtaining apparatus includes an electromagnetic wave generator; a sample holding unit which holds a sample to be tested and serves as a polarizer having a polarization axis which defines how an incident electromagnetic wave is to be divided according to a polarization state of the incident electromagnetic wave; an electromagnetic wave detecting unit which separately detects a transmitted electromagnetic wave transmitted through the sample holding unit and a reflected electromagnetic wave reflected off the sample holding unit, the transmitted and reflected electromagnetic waves being obtained by dividing the incident electromagnetic wave incident on the sample holding unit according to a relative positional relationship between the polarization state of the incident electromagnetic wave and the polarization axis of the sample holding unit; and a processor which processes signals of the electromagnetic waves detected by the electromagnetic wave detecting unit and obtains information about the sample.

16 Claims, 9 Drawing Sheets

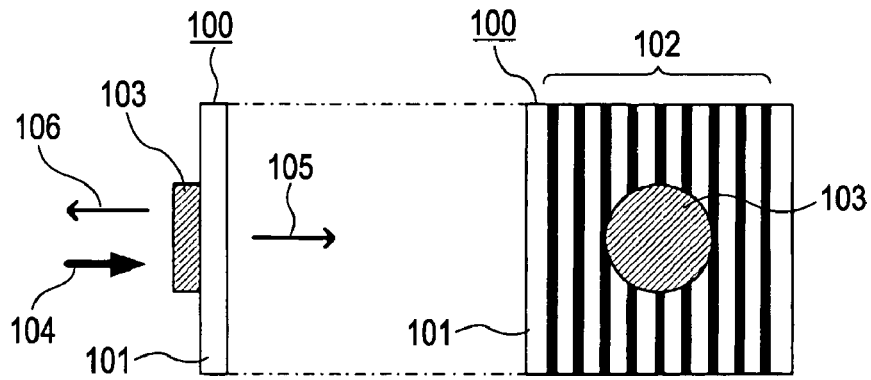
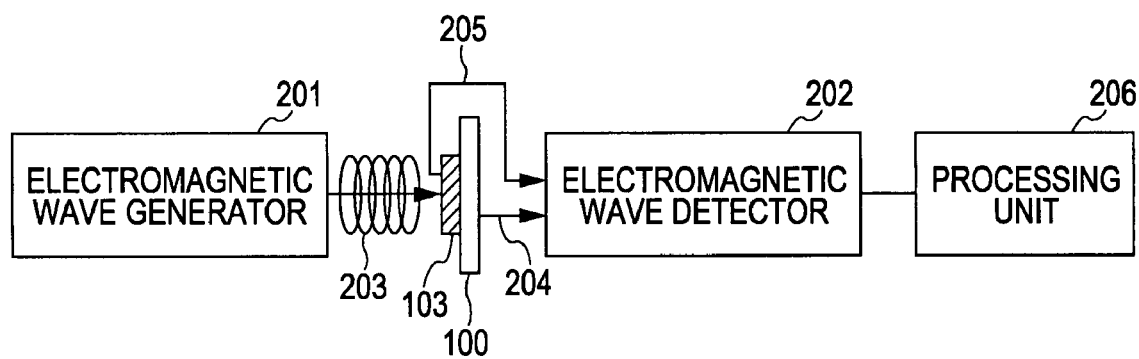

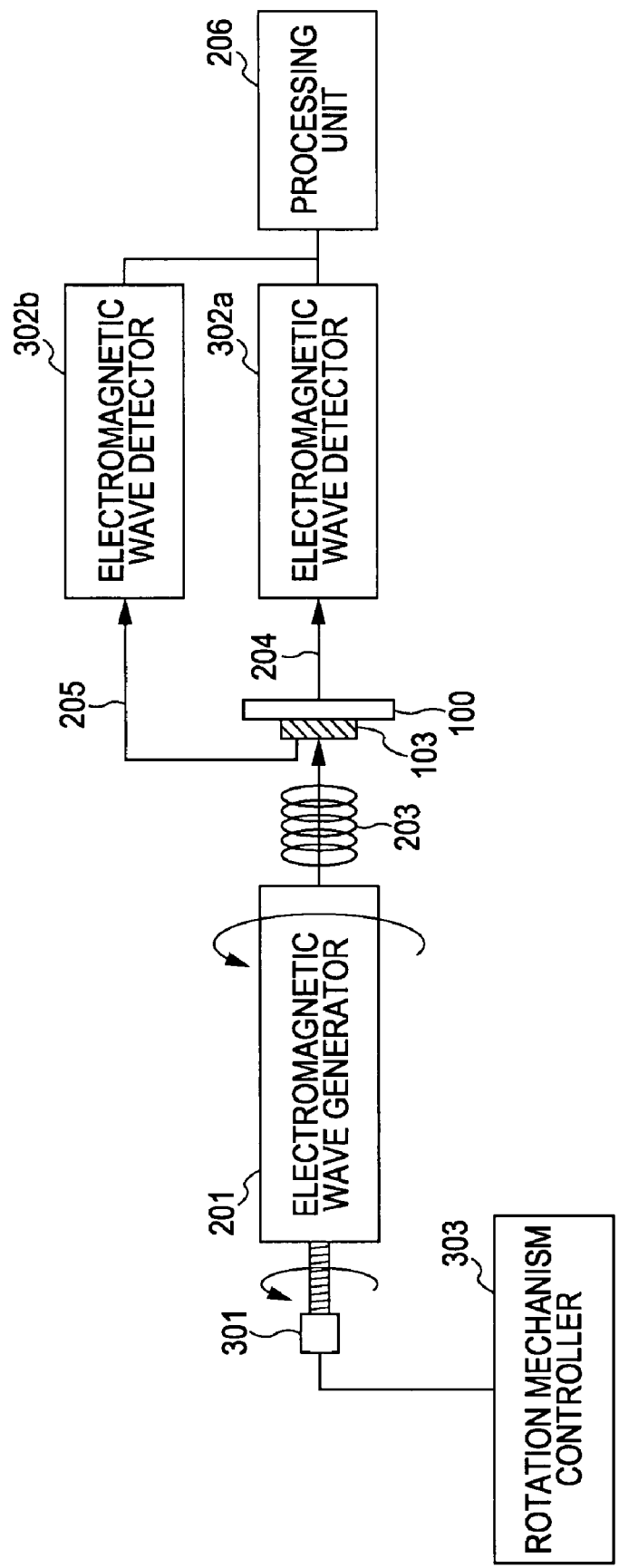

APPARATUS AND METHOD FOR OBTAINING SAMPLE INFORMATION BY DETECTING ELECTROMAGNETIC WAVE

BACKGROUND OF THE INVENTION

1. Field of the Invention

The present invention relates to sample information obtaining apparatuses and sample information obtaining methods for obtaining information about a sample by, for example, analyzing properties of the sample and performing imaging of the sample, using electromagnetic waves. In particular, the present invention relates to an apparatus and method for, for example, analyzing properties of a sample and performing imaging of the sample using high frequency electromagnetic waves in a millimeter to terahertz wave range.

2. Description of the Related Art

Recently, there have been developed nondestructive testing techniques using high frequency electromagnetic waves with frequencies in a millimeter to terahertz wave range (30 gigahertz (GHz) to 30 terahertz (Thz)). Such high frequency electromagnetic waves are referred to as terahertz waves in the present specification. Absorption lines of various materials, including biomolecules, are known to be present in terahertz waves. Examples of expected applications of the above-described frequency range include an imaging technique for performing a safe fluoroscopic examination as an alternative to an X-ray fluoroscopic examination; a spectroscopic technique for obtaining, for example, absorption spectra and complex permittivity of materials to examine molecular binding states and the like; an analyzing technique for analyzing biomolecules; and a technique for evaluating carrier concentrations and mobility.

Examples of such analyzing methods include a method for detecting a terahertz wave transmitted through test material (i.e., sample) and a method for detecting a terahertz wave reflected from a sample. From these detecting methods, an appropriate method is selected according to the type of properties the measurer wants to obtain. Conventionally, since these detecting methods often involve different optical arrangements, different apparatuses are developed for the respective methods. On the other hand, there is disclosed a technique in which each detecting method is performed by switching between optical systems in an apparatus whose entire structure is enclosed in a single housing (Japanese Patent Laid-Open No. 2004-191302).

This known technique provides a sample information obtaining apparatus including different optical systems for transmittance detection and reflectance detection. Since switching between these optical systems is performed to implement different detecting methods, a sample needs to be placed at a predetermined position appropriate for the detecting method to be implemented. Therefore, when both transmittance detection and reflectance detection are to be performed on one and the same sample, a time difference is made between measurements. For example, when a measurement for reflectance detection is to be performed after the completion of a measurement for transmittance detection, switching from one optical system to another is required and further, a sample needs to be moved from one position to another, accordingly. This takes a relatively long time to obtain information about the sample, and involves a relatively complex configuration of the apparatus.

SUMMARY OF THE INVENTION

A sample information obtaining apparatus, such as a sample analyzing apparatus, according to at least one exemplary embodiment of the present invention includes an electromagnetic wave generator configured to generate electromagnetic waves (which are typically terahertz waves), a sample holding unit, an electromagnetic wave detecting unit, and a processor. The sample holding unit is configured to provide a function of a polarizer having a polarization axis which defines how an incident electromagnetic wave is to be divided according to a polarization state of the incident electromagnetic wave, and is configured to hold a sample to be tested. The electromagnetic wave detecting unit is configured to separately detect a transmitted electromagnetic wave transmitted through the sample holding unit and a reflected electromagnetic wave reflected off the sample holding unit. The transmitted electromagnetic wave and the reflected electromagnetic wave are obtained by dividing the incident electromagnetic wave propagating from the electromagnetic wave generator and made incident on the sample holding unit, according to a relative positional relationship between the polarization state of the incident electromagnetic wave and the polarization axis of the sample holding unit. The processor is configured to process signals of the transmitted and reflected electromagnetic waves detected by the electromagnetic wave detecting unit and obtain information about the sample. With the configuration described above, transmittance measurement and reflectance measurement of the sample can be performed substantially simultaneously or concurrently. Additionally, the polarization state of the incident electromagnetic wave with respect to the polarization axis may be temporally varied, or may be fixed such that the incident electromagnetic wave has a component inclined with respect to the polarization axis.

A sample information obtaining method, such as a sample analyzing method, according to at least one exemplary embodiment of the present invention involves the following steps. In a first step, a sample to be tested is held on a sample holding unit configured to provide a function of a polarizer having a polarization axis which defines how an incident electromagnetic wave is to be divided according to a polarization state of the incident electromagnetic wave. In a second step, an electromagnetic wave (which is typically a terahertz wave) is made incident on the sample holding unit which holds the sample. In a third step, the incident electromagnetic wave is divided into a transmitted electromagnetic wave transmitted through the sample holding unit and a reflected electromagnetic wave reflected off the sample holding unit, according to a relative positional relationship between the polarization state of the incident electromagnetic wave and the polarization axis of the sample holding unit. In a fourth step, the transmitted electromagnetic wave and the reflected electromagnetic wave are separately detected, and in a fifth step, information about the sample is obtained on the basis of signals of the detected electromagnetic waves.

According to the sample information obtaining apparatus and method of the present invention, a function of the polarizer is added to the sample holding unit which holds the sample, and an electromagnetic wave incident on the sample is divided into the transmitted electromagnetic wave and the reflected electromagnetic wave, which are then separately detected. Therefore, transmitted and reflected electromagnetic waves of the sample can be measured in a relatively short period of time, for example, substantially simultaneously or concurrently. Moreover, during the interval between transmittance measurement and reflectance measurement, there is no need to perform switching between optical systems in the apparatus and also, there is no need to move the sample from one position to another. Therefore, it is made relatively easy to provide a compact apparatus with a simple configuration.

Further features of the present invention will become apparent from the following description of exemplary embodiments with reference to the attached drawings.

BRIEF DESCRIPTION OF THE DRAWINGS

FIG. 1A and FIG. 1B are schematic diagrams illustrating a testing device according to at least one exemplary embodiment of the present invention.

FIG. 2 is a schematic diagram illustrating a sample information obtaining apparatus (or analyzing apparatus) according to at least one exemplary embodiment of the present invention.

FIG. 3 is a schematic diagram illustrating a sample information obtaining apparatus (or analyzing apparatus) according to a first exemplary embodiment of the present invention.

DESCRIPTION OF THE EMBODIMENTS

Figure 4:
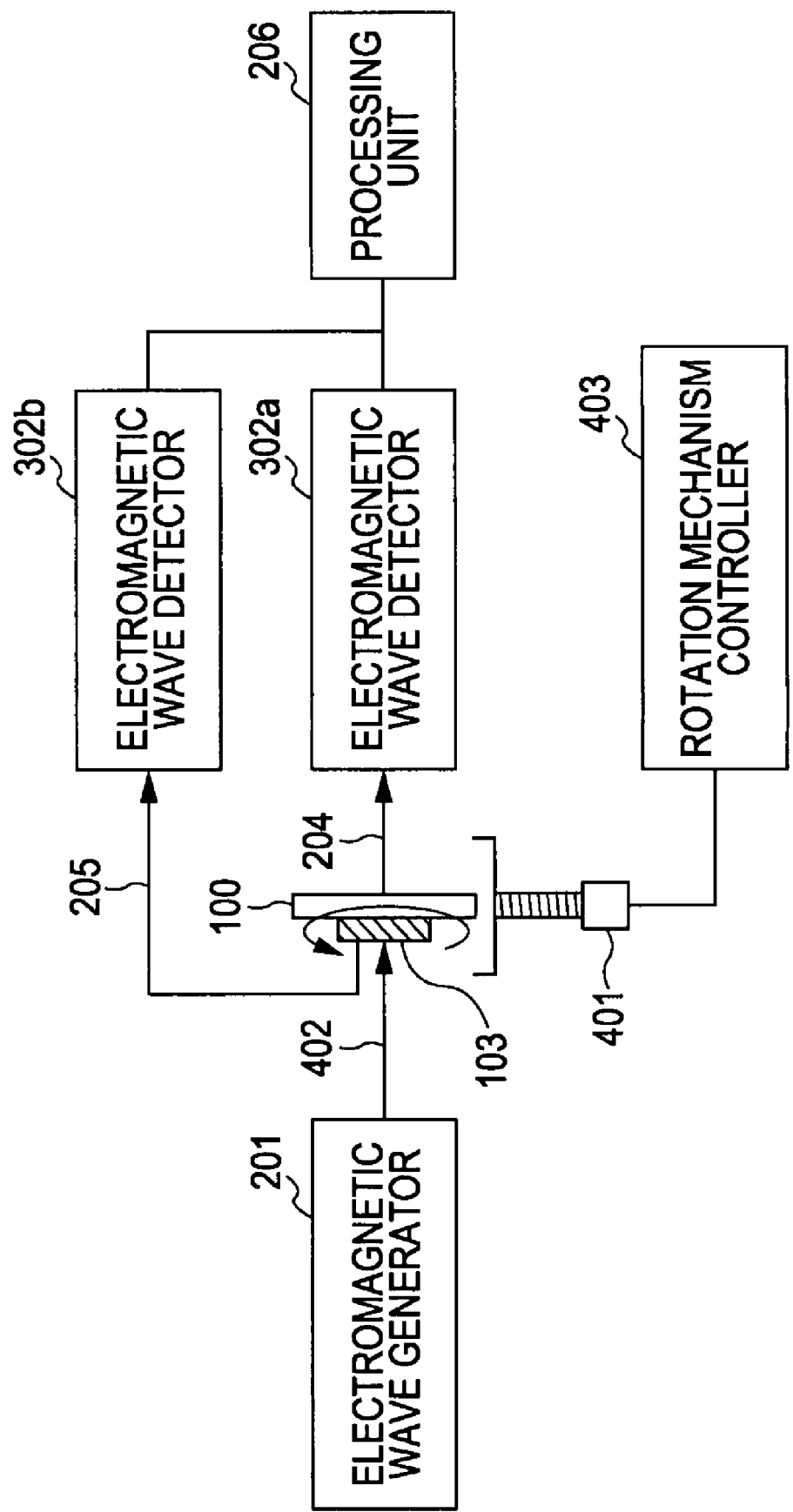
FIG. 4 is a schematic diagram illustrating a sample information obtaining apparatus (or analyzing apparatus) according to a second exemplary embodiment of the present invention.

Exemplary embodiments of the present invention will now be described with reference to the drawings. Identical elements are given the same reference numerals throughout the drawings.

FIGS. 1A and 1B are schematic diagrams illustrating a testing device of a sample information obtaining apparatus according to at least one exemplary embodiment of the present invention. FIGS. 1A and 1B are a side view and a top view of the testing device, respectively. As illustrated in FIGS. 1A and 1B, in a testing device 100 of the present exemplary embodiment, a sample holding unit 101 for holding a sample 103 to be tested includes a polarizer 102. A polarizer has a polarization axis which defines, according to a polarization state, how an incident electromagnetic wave is to be divided. Here, the sample 103 is placed on and held by the sample holding unit 101 and irradiated with an electromagnetic wave (incident electromagnetic wave 104). By detecting changes in the propagation state of the incident electromagnetic wave 104, the properties of the sample 103 are measured. The polarizer 102 is capable of transmitting a polarization component having a magnetic field component parallel to the polarization axis of the polarizer 102, and is also capable of reflecting a polarization component having a magnetic field component orthogonal to the polarization axis of the polarizer 102.

For example, when the incident electromagnetic wave 104 has a certain polarization component, the incident electromagnetic wave 104 is divided into a transmitted electromagnetic wave 105 and a reflected electromagnetic wave 106 according to a relative relationship between the polarization direction of the incident electromagnetic wave 104 and the polarization axis of the polarizer 102. The polarization state of the incident electromagnetic wave 104 with respect to the polarization axis is fixed such that the incident electromagnetic wave 104 has a component inclined with respect to the polarization axis. More specifically, when a wire grid is used as the polarizer 102, a polarization component having an electric field component orthogonal to the axial direction of wires is transmitted, as the transmitted electromagnetic wave 105, through the polarizer 102. On the other hand, a polarization component having an electric field component parallel to the axial direction of wires is reflected, as the reflected electromagnetic wave 106, from the polarizer 102. By individually detecting these electromagnetic waves, transmittance measurement and reflectance measurement in an incident area of the incident electromagnetic wave 104 can be substantially simultaneously performed.

Referring to FIG. 1B, the polarizer 102 extends over the entire area of the sample holding unit 101. However, the configuration of the polarizer 102 is not limited to this. For example, the polarizer 102 may be provided only in part of the sample holding unit 101, as long as the structure of the polarizer 102 is present in an area occupied by the incident electromagnetic wave 104 incident on the sample 103.

Referring to FIG. 1A, the sample 103 is irradiated with the incident electromagnetic wave 104 from a side opposite the sample holding unit 101. Alternatively, the sample 103 may be irradiated from a side adjacent to the sample holding unit 101, that is, from the underside of the sample 103. Even in that case, the incident electromagnetic wave 104 at least penetrates into and is reflected off the sample 103. Therefore, the propagation state of the reflected electromagnetic wave 106 is changed by the effect of the sample 103.

Also, the configuration of the polarizer 102 is not limited to that of the wire grid described above. For example, the polarizer 102 may have a structure in which molecules of organic substances are aligned as in the case of liquid crystal. In other words, the polarizer 102 may have any structure with a refractive index that varies periodically in a specific direction (either in a square wave pattern with abrupt changes or in a sine wave pattern with gradual changes).

Additionally, while the incident electromagnetic wave 104 is substantially perpendicularly incident on the surface of the sample 103 as illustrated in FIG. 1A, the incident electromagnetic wave 104 may be incident on the surface of the sample 103 at any angle, as long as the transmitted electromagnetic wave 105 and the reflected electromagnetic wave 106 can be produced.

Figure 10A:
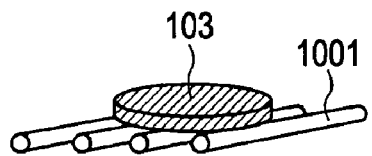
FIGS. 10A to 10D illustrate exemplary configurations of a testing device of an apparatus according to at least one exemplary embodiment of the present invention.
Figure 10B:
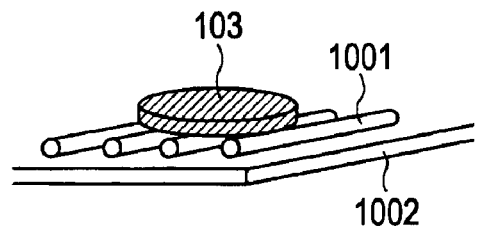
Figure 10C:
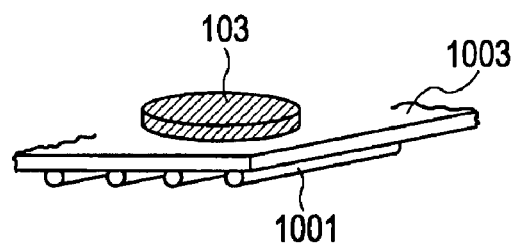
Figure 10D:
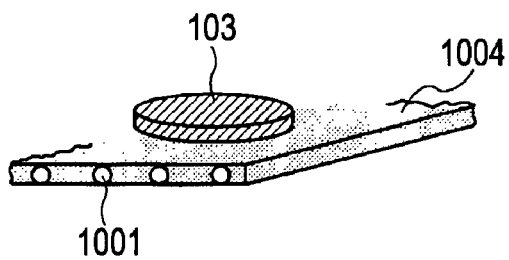

FIGS. 10A to 10D illustrate different configurations of the sample holding unit 101 in which a wire grid 1001 is used as the polarizer 102. As illustrated in FIG. 10A, the wire grid 1001 itself may be used as the sample holding unit 101 for holding the sample 103. The configuration of the sample holding unit 101 is not limited to this. For example, as illustrated in FIG. 10B, the wire grid 1001 may be secured to the upper surface of a lower member 1002 to form the sample holding unit 101, which holds the sample 103. Also, as illustrated in FIG. 10C, an upper member 1003 may be disposed on the wire grid 1001 to form the sample holding unit 101, which holds the sample 103. Furthermore, as illustrated in FIG. 10D, spaces between adjacent wires of the wire grid 1001 may be filled with a filling member 1004 to form the sample holding unit 101, which holds the sample 103. As described above, the polarizer 102 may be configured in any manner as long as it is disposed immediately below or close to the sample 103.

For the use of electromagnetic waves, it is desirable that the lower member 1002, the upper member 1003, and the filling member 1004 be made of transparent material. For example, a quartz substrate made of highly crystalline Z-cut quartz and a semiconductor substrate made of high resistance silicon or the like can be used. The filling member 1004 can be made of resin material, such as polyolefin resin.

Figure 11:
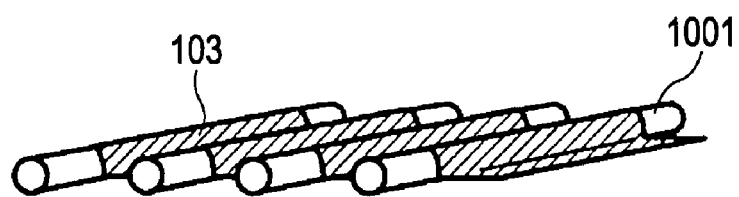
FIG. 11 illustrates an exemplary configuration of a testing device of an apparatus according to at least one exemplary embodiment of the present invention.

In the configurations of FIGS. 10A to 10D, the sample 103 and the wire grid 1001, and the sample 103 and each of the above-described members are clearly separate from each other. However, the configuration of the sample holding unit 101 is not limited to this. For example, as illustrated in FIG. 11, spaces between adjacent wires of the wire grid 1001 may be filled with the sample 103 that is fluid. It is also possible that the sample 103 infiltrates into the members illustrated in FIGS. 10A to 10D. Examples of materials that allow infiltration of the sample 103 include fabric members and porous members with fine holes.

FIG. 2 is a schematic diagram illustrating a sample information obtaining apparatus according to at least one exemplary embodiment of the present invention. The sample information obtaining apparatus of FIG. 2 includes the testing device 100 configured as described above. FIG. 2 illustrates an analyzing apparatus as an example of the sample information obtaining apparatus. As illustrated in FIG. 2, the analyzing apparatus includes an electromagnetic wave generator 201, the testing device 100 including the sample holding unit 101 of FIGS. 1A and 1B, an electromagnetic wave detector 202, and a processing unit 206.

The electromagnetic wave generator 201 generates and applies an electromagnetic wave to the sample 103 held by the testing device 100. In particular, the electromagnetic wave used in the present invention is a terahertz wave. In the present exemplary embodiment, the polarization direction (polarization state) of a terahertz wave generated from the electromagnetic wave generator 201 rotates relative to the polarization axis of the polarizer 102 included in the testing device 100. Therefore, the terahertz wave generated from the electromagnetic wave generator 201 can be regarded as a circularly polarized signal 203 illustrated in FIG. 2.

The terahertz wave can be generated, for example, using an antenna structure formed on a semiconductor substrate. The semiconductor substrate used in the present exemplary embodiment is a gallium arsenide (GaAs) substrate measuring 100 μm in thickness and having a low-temperature gallium arsenide (LT-GaAs) epitaxial growth layer with a thickness of 1.5 μm at its surface. The antenna structure used in the present exemplary embodiment is a dipole antenna structure with a 5-μm gap in the center thereof. The dipole antenna structure has an antenna length of 30 μm and is produced using gold (AuGe/Ni/Au) by a typical evaporation process.

In this case, the polarization direction of a terahertz wave generated from the antenna is defined by the orientation of the dipole axis of the antenna structure. Therefore, to form this terahertz wave signal into the circularly polarized signal 203, it is necessary to provide a mechanism, such as a quarter (¼) wave plate, for controlling the polarization state using an optical system (not shown). A method for controlling the polarization state is not limited to this. For example, control may be performed such that a relative positional relationship between the polarization direction of a terahertz wave generated from the electromagnetic wave generator 201 and the polarization axis direction of the polarizer 102 included in the testing device 100 is changed. To perform such control, a mechanism (not shown) for mechanically rotating either the electromagnetic wave generator 201 or the testing device 100 may be used. In some cases, a method for simultaneously controlling both the electromagnetic wave generator 201 and the testing device 100 may be used. This method allows fine and subtle adjustment of the polarization state described above.

Also, the antenna structure is not limited to that described above. The size and shape of the antenna vary depending on the frequency characteristics and polarization characteristics of electromagnetic waves to be used. For example, if a spiral antenna structure is used, a terahertz wave generated from the antenna is formed into the circularly polarized signal 203.

Terahertz waves used in the present exemplary embodiment are generated by biasing the gap of the above-described dipole antenna and optically gating the gap using femtosecond laser pulses. However, the method for generating terahertz waves is not limited to this. A possible method is to perform gating using a difference frequency between two types of laser beams with different wavelengths. Another possible method is to use a negative resistance element, such as a quantum-cascade laser device or a resonant tunneling diode. It is also possible to use a method in which an oscillator using nonlinear optical crystal or an oscillator using an electron tube, such as a backward-wave oscillator (BWO), is used.

Figure 7:
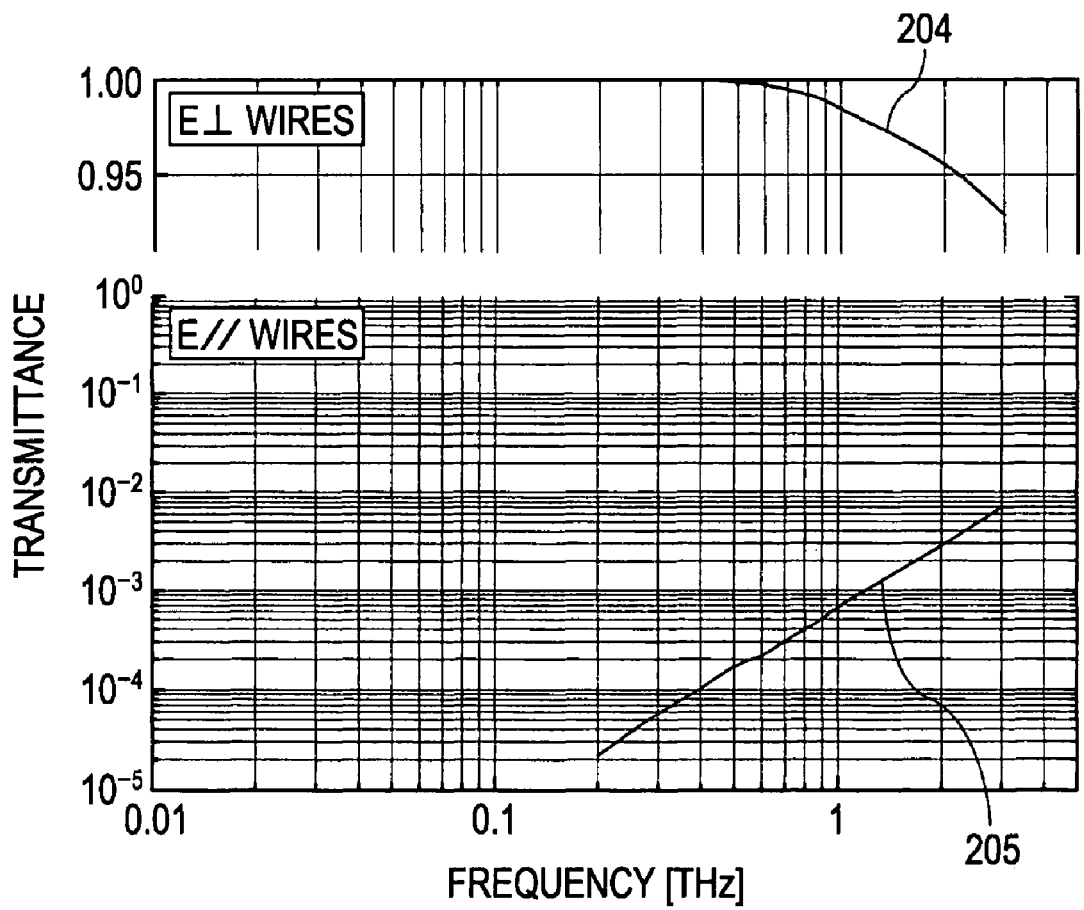
FIG. 7 illustrates exemplary frequency characteristics of a wire grid.

The circularly polarized signal 203 obtained in the way described above is applied to the sample 103 in the testing device 100. Next, the operation of the circularly polarized signal 203 will be described. Here, the wire grid 1001 is used as the polarizer 102 for the testing device 100. FIG. 7 is a graph showing overall frequency characteristics of the wire grid 1001. The wire grid 1001 is made of, for example, tungsten wires measuring 10 μm in diameter and spaced at 25-μm grid intervals. As shown in FIG. 7, if an electromagnetic wave signal has a frequency of up to several terahertz (Thz), a terahertz wave having an electric field component orthogonal to the polarization axis (orthogonal polarization component signal 204) is transmitted through the wire grid 1001, while a terahertz wave having an electric field component parallel to the polarization axis (parallel polarization component signal 205) is reflected off the wire grid 1001.

The orthogonal polarization component signal 204 here is equivalent to the transmitted electromagnetic wave 105 of FIG. 1, and the parallel polarization component signal 205 here is equivalent to the reflected electromagnetic wave 106 of FIG. 1. In the present exemplary embodiment, particularly when the wire grid 1001 is used as the polarizer 102, such expressions as "orthogonal polarization component signal 204" and "parallel polarization component signal 205" are used. The frequency characteristics of the wire grid 1001 are not limited to those illustrated in FIG. 7 and may vary depending on the material used, diameter of wires, and grid intervals.

The plane of polarization of the above-described terahertz wave rotates relative to the polarization axis of the polarizer 102, but the configuration is not limited to this. For example, the terahertz wave may be linearly polarized in the plane of polarization. If the polarization direction of an incident terahertz wave is controlled to be inclined 45 degrees with respect to the polarization axis of the wire grid 1001, the incident terahertz wave can branch off in different directions. Also, the angle of the linearly polarized wave with respect to the polarization axis of the wire grid 1001 is not limited to 45 degrees. If the branching ratio between the transmitted electromagnetic wave 105 and the reflected electromagnetic wave 106 is changed by the presence of the sample 103, this angle may be adjusted to balance the branching ratio. When there is no need to balance the branching ratio between the transmitted electromagnetic wave 105 and the reflected electromagnetic wave 106, even if the above-described angle is changed from 45 degrees to some other value, it is still possible to perform an operation similar to that described above.

The electromagnetic wave detector 202 detects the orthogonal polarization component signal 204 and the parallel polarization component signal 205 separately. While FIG. 2 illustrates the electromagnetic wave detector 202 as a single entity, there may be provided a plurality of electromagnetic wave detectors. For example, the electromagnetic wave detector 202 detects a terahertz wave in the following manner. Here, the electromagnetic wave detector 202 has a similar configuration to that of the electromagnetic wave generator 201. The electromagnetic wave detector 202 biases a gap of an antenna, optically gates the gap using femtosecond laser pulses, and thereby detects a terahertz wave. The intensity of the terahertz wave at a given point at the moment when the gap is gated with the femtosecond laser pulses is detected here. By sweeping the timing of the gating, time-domain terahertz waves can be obtained. The method for detecting a terahertz wave is not limited to this. For example, a thermal detector, such as a bolometer, or electro-optical effects may be used for the detection. A semiconductor device, such as a Schottky diode, may also be used for the detection.

Figure 8:
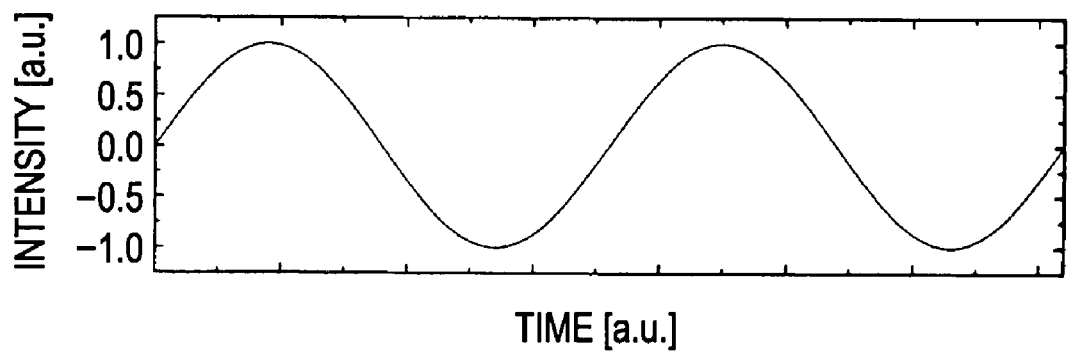
FIG. 8 is a conceptual diagram illustrating exemplary operation of a terahertz wave transmitted through or reflected from a testing device of an apparatus according to at least one exemplary embodiment of the present invention.

In the present exemplary embodiment, a terahertz wave incident on the sample 103 is the circularly polarized signal 203 having a polarization direction changing relative to the polarization axis of the polarizer 102. Therefore, as shown in FIG. 8, the intensity of the orthogonal polarization component signal 204 and parallel polarization component signal 205 derived from the circularly polarized signal 203 changes with time (while there is a temporal phase shift of 90 degrees therebetween). Currently, it is difficult to obtain terahertz electromagnetic waves in real time. Therefore, a chopper or the like has been conventionally used to modulate and detect a terahertz wave. However, in the present exemplary embodiment, as shown in FIG. 8, the intensity of a terahertz wave having passed through the sample 103 is modulated by the polarizer 102. Therefore, a modulation mechanism such as a chopper that has been conventionally used for such modulation is no longer needed. This can simplify the configuration of the apparatus and reduce the size thereof. Additionally, detection of a terahertz wave with modulated intensity enables detection of a small signal.

Figure 12:
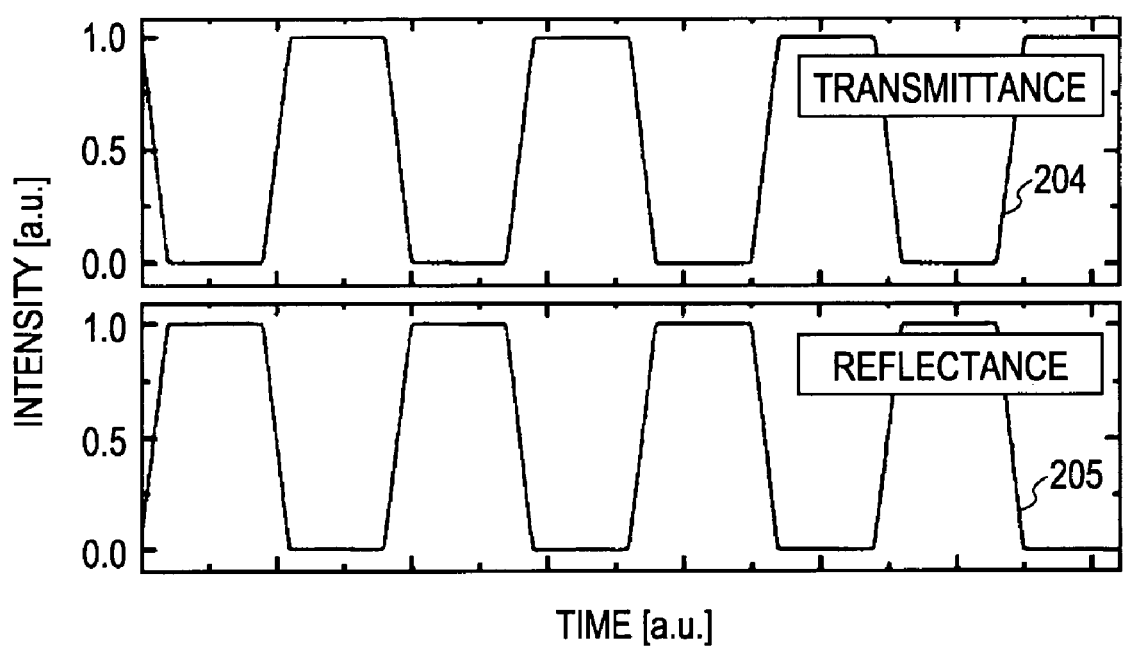
FIG. 12 is a conceptual diagram illustrating an exemplary operation of a terahertz wave transmitted through or reflected from a testing device of an apparatus according to at least one exemplary embodiment of the present invention.

Referring to FIG. 8, the intensity of the orthogonal polarization component signal 204 and parallel polarization component signal 205 continuously changes in a sine wave pattern. However, the pattern of change in intensity is not limited to this. For example, if the mechanical rotation mechanism described above is provided to allow switching of the polarization direction of a terahertz wave between orthogonal and parallel directions relative to the polarization axis, a square wave pattern shown in FIG. 12 is produced. As shown in FIG. 12, the orthogonal polarization component signal 204 and the parallel polarization component signal 205 provide complementary square waves. Additionally, by controlling the rotation of the rotation mechanism described above, an intensity change in a desired pattern, such as a triangular wave pattern, can be obtained.

The processing unit 206 uses terahertz wave signals obtained at the electromagnetic wave detector 202 to analyze the properties of the sample 103. For example, the processing unit 206 uses signals obtained from the electromagnetic wave detector 202 to generate time-domain terahertz waves. Then, the processing unit 206 converts the terahertz waves into a frequency-domain intensity spectrum to obtain frequency characteristics of the sample 103. Thus, for example, by analyzing changes in phase and intensity resulting from the presence or absence of the sample 103, various properties of the sample 103, such as a complex index of refraction and the like, can be obtained. It is desirable here that the processing unit 206 obtains, in advance, a signal in a state where the sample 103 is not present so that the obtained signal can be used as a reference signal. If the sample 103 is a biomolecule, such as deoxyribonucleic acid (DNA), a protein, or an amino acid, it is possible to detect changes in the structure and properties of the sample 103, as well as the presence or absence of the sample 103. Additionally, if the processing unit 206 has a database on the sample 103, it is possible to identify the sample 103 by comparing a measurement result with data stored in the database.

Thus, in the present exemplary embodiment where the sample holding unit 101 includes the polarizer 102, transmittance measurement and reflectance measurement that have been conventionally performed individually can be performed simultaneously or concurrently. Therefore, even when a property of the sample 103 or measurement environment changes with time, transmittance and reflectance can be measured under substantially the same conditions. Moreover, since transmittance measurement and reflectance measurement are performed simultaneously, they can be performed concurrently at exactly the same position.

Additionally, a scanning mechanism (not shown) may scan the sample 103 with a terahertz wave applied thereto. Examples of the scanning mechanism include an actuator that moves the testing device 100 or the electromagnetic wave generator 201, and an optical system that optically changes the optical path of a terahertz wave generated from the electromagnetic wave generator 201. Also, the directivity of a terahertz wave generated from the electromagnetic wave generator 201 may be controlled. That is, any method can be used as long as the position of a terahertz wave incident on the sample 103 is varied relative to the sample 103, in a direction of a plane of the sample 103 intersecting the incident direction of an incident electromagnetic wave (e.g., in a direction of a plane orthogonal to the incident direction).

By scanning a sample with a terahertz wave using a method such as that described above, a transmitted image and a reflected image can be simultaneously obtained in the present exemplary embodiment. These transmitted and reflected images are obtained at exactly the same point of the sample. On the other hand, if, for example, transmitted and reflected images individually obtained are to be compared with each other, it is necessary to perform alignment of these images before comparison. Since such transmitted and reflected images can be simultaneously obtained in the present exemplary embodiment, the process of alignment can be omitted and thus, the speed of measurement can be increased.

Figure 9:
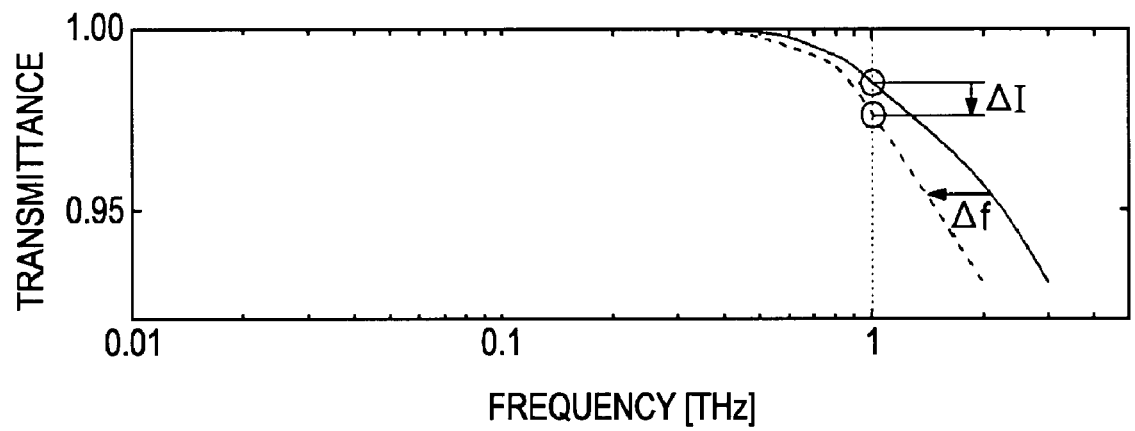
FIG. 9 illustrates an exemplary operation performed when an apparatus according to at least one exemplary embodiment of the present invention is used as a trace detecting apparatus.

The frequency characteristics of the polarizer 102 are changed by the presence of material near the polarizer 102. This is caused by the fact that the refractive index in an area around the polarizer 102 is changed. This fact can be used, for example, in detection performed by a trace detector, which detects a change in refractive index caused by the presence of the sample 103 near the polarizer 102 as a change in the frequency characteristics of the polarizer 102. As shown in FIG. 9, when a detection frequency is fixed (at 1 THz in FIG. 9), monitoring a change ΔI in the transmittance intensity of a terahertz wave allows trace detection of the sample 103. Alternatively, as shown in FIG. 9, when transmittance intensity to be detected is fixed at a certain value, monitoring a change Δf in frequency corresponding to the desired transmittance intensity allows trace detection of the sample 103.

As described above, in the apparatus and method of the present exemplary embodiment, the function of a polarizer is added to a sample stage by which a sample is held, an electromagnetic wave incident on the sample is divided into a transmitted electromagnetic wave and a reflected electromagnetic wave, which are then individually detected. As a result, since transmittance measurement and reflectance measurement of the sample can be performed simultaneously, the time required for measurement can be reduced. Moreover, since there is no need to provide different optical systems for transmittance measurement and reflectance measurement, the size of the entire apparatus can be reduced.

When the present exemplary embodiment is applied to an imaging apparatus, transmission imaging and reflection imaging can be performed simultaneously. This allows easy comparison of the imaging results. Moreover, since transmittance measurement and reflectance measurement are performed simultaneously on the same sample, there is no need to consider temporal changes in properties of the sample and measurement environment. Since comparison of the results of transmittance measurement and reflectance measurement can be made without consideration of differences among samples and changes in experimental conditions, experimental accuracy can be improved.

On the other hand, in the conventional technique described above, if a test object is an object, such as a biomolecule, that is subject to temporal changes in measurement environment and its own properties (e.g., temporal changes in moisture content and activity state), the properties of the test object may be changed during the time required for switching between detecting systems. To reduce the time required for such a switching operation, a plurality of the same test objects may be placed at predetermined positions in advance. However, in a strict sense, this is not equivalent to measurement performed on one and the same test object. For example, if the conditions of the plurality of test objects placed at respective positions are different for some reason, it is difficult for the measurer who performs the measurement to immediately recognize the differences. This results in degradation in data reliability.

When imaging of a test object is to be performed according to the principles of spectroscopic analysis by a conventional apparatus which performs transmission imaging and reflection imaging by switching between optical systems, a position at which the test object is placed for one optical system is different from that for another optical system. That is, a position at which transmission imaging is performed is different from a position at which reflection imaging is performed. For example, to obtain a transmitted image and a reflected image of a specific portion of the test object, it is necessary to move the test object from one position to another. Therefore, it is difficult to achieve alignment of these images.

EXEMPLARY EMBODIMENTS

Hereinafter, exemplary embodiments of the present invention will be more specifically described with reference to the drawings.

First Exemplary Embodiment

FIG. 3 illustrates a first exemplary embodiment of the present invention. The present exemplary embodiment provides a method for obtaining a circularly polarized signal. As illustrated in FIG. 3, an analyzing apparatus of the present exemplary embodiment includes a rotation mechanism 301 and a rotation mechanism controller 303 which control a polarization state for obtaining the circularly polarized signal 203. In the present exemplary embodiment, there are two electromagnetic wave detectors 302a and 302b as illustrated in FIG. 3.

The rotation mechanism 301 is an actuator for rotating the electromagnetic wave generator 201 about the axis of the propagation direction of a terahertz wave. When a terahertz wave from the electromagnetic wave generator 201 has a polarization component in a specific direction, the polarization direction of the terahertz wave to be incident on the sample 103 held by the testing device 100 can be rotated by mechanically rotating this polarization component. The rotation mechanism controller 303 is a driver for controlling the rotation speed of the rotation mechanism 301. In the present exemplary embodiment, the intensity of the orthogonal polarization component signal 204 transmitted through the testing device 100 and the intensity of the parallel polarization component signal 205 reflected off the testing device 100 are modulated with this rotation frequency as shown in FIG. 8. For example, performing lock-in detection with this modulation frequency allows detection of a small terahertz wave signal.

In the present exemplary embodiment, a polarized terahertz wave generated from the electromagnetic wave generator 201 has a linear polarization component. However, the polarized terahertz wave may have, for example, a circular polarization component. In this case, the rotation frequency of the polarized wave of the circularly polarized signal 203 is made variable by the rotation mechanism 301 and the rotation mechanism controller 303. This is equivalent to the adjustment of the modulation frequency of modulation signals described above.

Such adjustment of the modulation frequency provides a frequency at which maximum detection sensitivity for the analyzing apparatus can be achieved.

Of the two electromagnetic wave detectors of the present exemplary embodiment, the electromagnetic wave detector 302a detects the orthogonal polarization component signal 204 transmitted through the testing device 100, while the electromagnetic wave detector 302b detects the parallel polarization component signal 205 reflected from the testing device 100. The processing unit 206 uses these detected signals to analyze the properties of the sample 103.

With the above-described configuration of the present exemplary embodiment, transmittance measurement and reflectance measurement of the sample 103 can be simultaneously performed. Also, when the scanning mechanism (not shown) scans the sample 103 with a terahertz wave incident on the sample 103, a transmitted image and reflected image of the sample 103 can be obtained simultaneously.

Second Exemplary Embodiment

FIG. 4 illustrates a second exemplary embodiment of the present invention. The present exemplary embodiment provides another method for obtaining a circularly polarized signal. As illustrated in FIG. 4, an analyzing apparatus of the present exemplary embodiment includes a rotation mechanism 401 and a rotation mechanism controller 403 which control a polarization state for obtaining the circularly polarized signal. In the present exemplary embodiment, there are also two electromagnetic wave detectors 302a and 302b as illustrated in FIG. 4.

The rotation mechanism 401 is an actuator for rotating the testing device 100 about the axis of the propagation direction of a terahertz wave. When the electromagnetic wave generator 201 generates an electromagnetic wave signal 402 having a polarization component in a specific direction, the polarization direction of the terahertz wave to be incident on the sample 103 is rotated by rotating the testing device 100. A circularly polarized signal can thus be obtained. The rotation mechanism controller 403 is a driver for controlling the rotation speed of the rotation mechanism 401. In the present exemplary embodiment, the intensity of the orthogonal polarization component signal 204 transmitted through the testing device 100 and the intensity of the parallel polarization component signal 205 reflected off the testing device 100 are modulated with this rotation frequency as shown in FIG. 8. Again, performing lock-in detection with this modulation frequency allows detection of a small terahertz wave signal.

In the present exemplary embodiment, a polarized wave of the electromagnetic wave signal 402 generated from the electromagnetic wave generator 201 has a linear polarization component. However, the polarized wave of the electromagnetic wave signal 402 may have, for example, a circular polarization component. In this case, the rotation frequency of the polarized wave having the circular polarization component is made variable by the rotation mechanism 401 and the rotation mechanism controller 403. This is equivalent to the adjustment of the modulation frequency of modulation signals described above. Such adjustment of the modulation frequency provides a frequency at which maximum detection sensitivity for the analyzing apparatus can be achieved.

In the present exemplary embodiment, there are also two electromagnetic wave detectors. The electromagnetic wave detector 302a detects the orthogonal polarization component signal 204 transmitted through the testing device 100, while the electromagnetic wave detector 302b detects the parallel polarization component signal 205 reflected from the testing device 100. The processing unit 206 uses these detected signals to analyze the properties of the sample 103.

In the present exemplary embodiment, transmittance measurement and reflectance measurement of the sample 103 can be performed simultaneously. Also, when the scanning mechanism (not shown) scans the sample 103, a transmitted image and reflected image of the sample 103 can be obtained simultaneously.

Third Exemplary Embodiment

Figure 5:
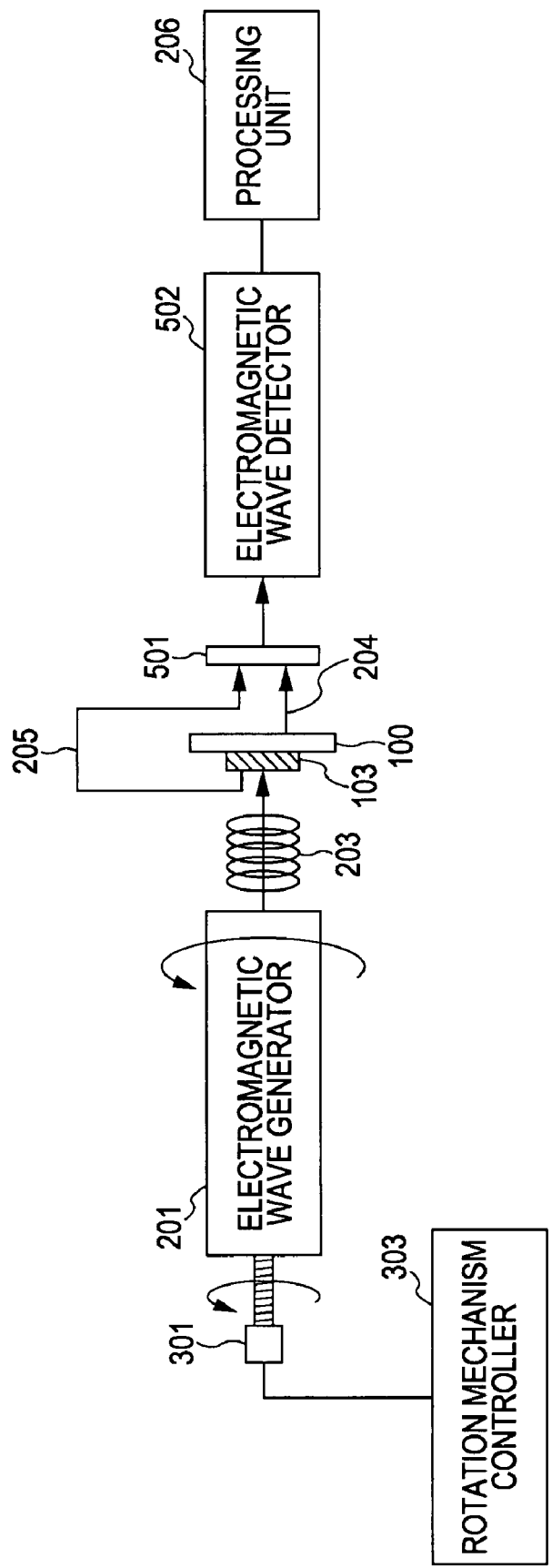
FIG. 5 is a schematic diagram illustrating a sample information obtaining apparatus (or analyzing apparatus) according to a third exemplary embodiment of the present invention.

FIG. 5 illustrates a third exemplary embodiment of the present invention. The present exemplary embodiment provides a method for detecting an electromagnetic wave. An apparatus of the present exemplary embodiment is similar in certain aspects to the analyzing apparatus of the first exemplary embodiment. Therefore, parts and features that are common to those of the first exemplary embodiment will not be described here.

FIG. 5 is a schematic diagram illustrating an analyzing apparatus of the present exemplary embodiment. As illustrated in FIG. 5, the analyzing apparatus of the present exemplary embodiment is obtained by adding a selection mechanism 501 to the analyzing apparatus of the first exemplary embodiment. Additionally, an electromagnetic wave detector 502 is provided downstream of the selection mechanism 501.

Figure 13A:
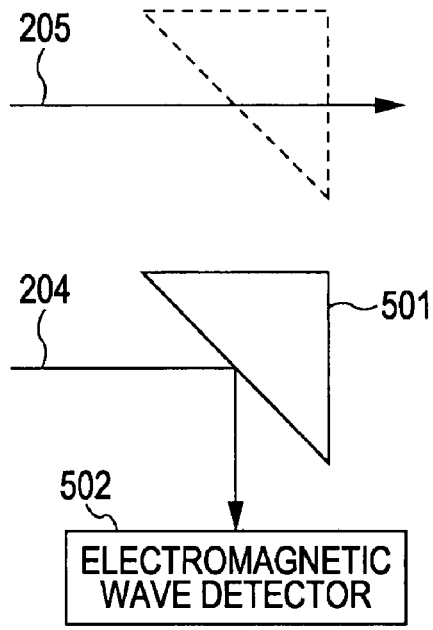
FIG. 13A and FIG. 13B illustrate an exemplary configuration of a selection mechanism of an apparatus according to at least one exemplary embodiment of the present invention.
Figure 13B:
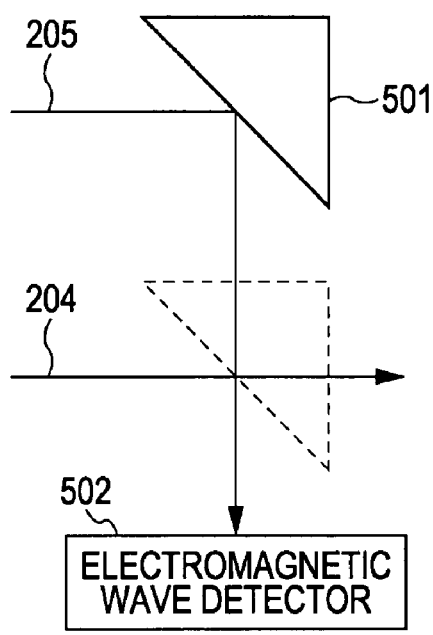

The selection mechanism 501 sequentially selects the orthogonal polarization component signal 204 transmitted through the testing device 100 and the parallel polarization component signal 205 reflected from the testing device 100 and allows the selected signals to be input to the electromagnetic wave detector 502. Terahertz waves are in the frequency range where they can be optically controlled. Therefore, the selection mechanism 501 includes a mirror and an actuator so that the optical path can be mechanically moved. FIGS. 13A and 13B illustrate a configuration of the selection mechanism 501. FIG. 13A illustrates a state where the orthogonal polarization component signal 204 is reflected off the mirror (having been moved downward by the actuator) and input to the electromagnetic wave detector 502. FIG. 13B illustrates a state where the parallel polarization component signal 205 is reflected off the mirror (having been moved upward by the actuator) and input to the electromagnetic wave detector 502. Any other method that can sequentially select signals of different polarization components can be used.

Referring back to FIG. 5, the processing unit 206 receives signals output from the electromagnetic wave detector 502 and processes the received signals of different polarization components separately, with reference to the switching timing of the selection mechanism 501.

By using the selection mechanism 501 as described above, the number of electromagnetic wave detectors can be reduced and thus, the size of the apparatus can be reduced. Moreover, since one and the same detecting element is used to compare measurements, the reliability of the measurement result can be improved. Also, since the number of detecting elements can be reduced, a low-cost apparatus can be provided. In particular, since a signal of each polarization component is detected by switching the selection mechanism 501, multiple tasks of the testing device 100 can be easily performed by a small number of components of the apparatus.

With the above-described configuration of the present exemplary embodiment, transmittance measurement and reflectance measurement of the sample 103 can be performed substantially simultaneously or concurrently. Also, when the scanning mechanism (not shown) scans the sample 103 with a terahertz wave incident on the sample 103, a transmitted image and reflected image of the sample 103 can be obtained substantially simultaneously.

Fourth Exemplary Embodiment

Figure 6:
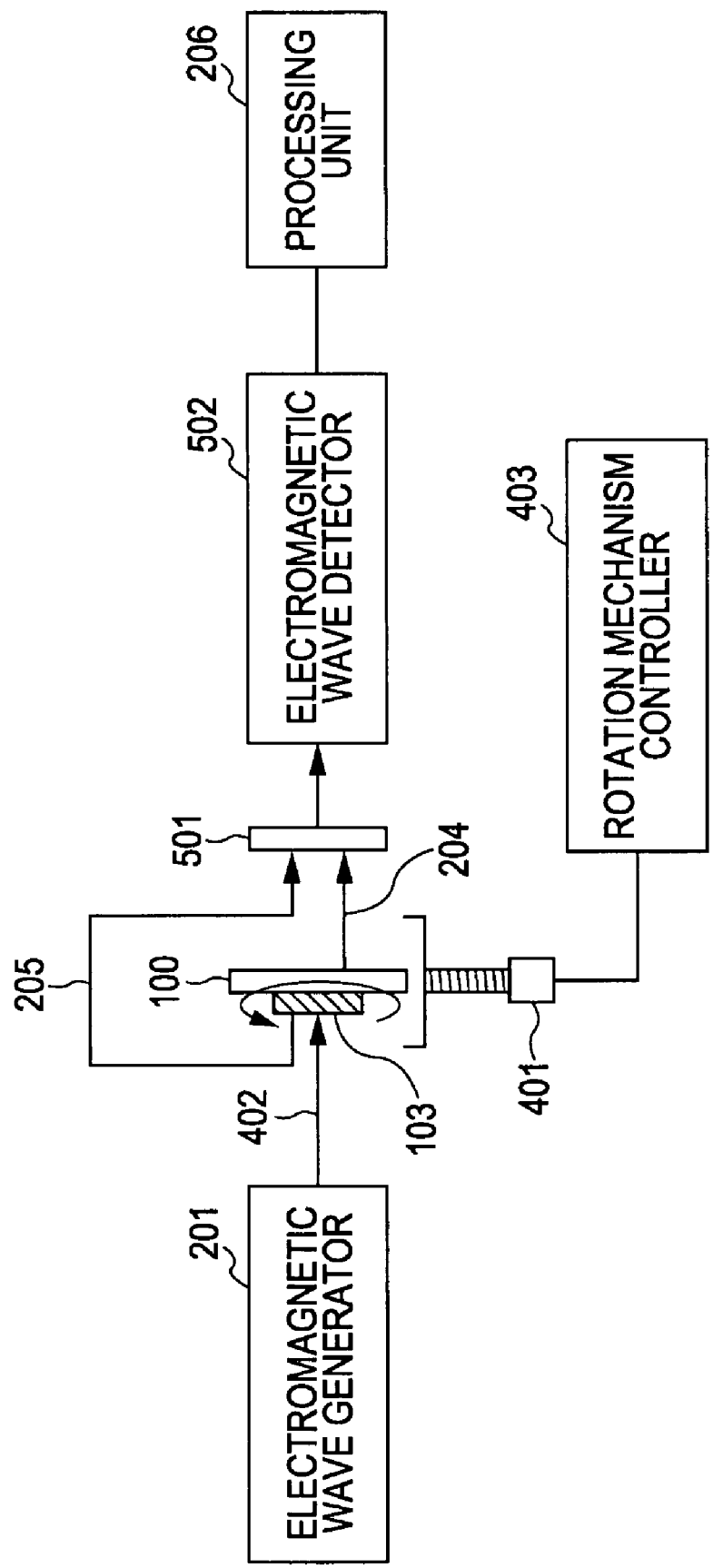
FIG. 6 is a schematic diagram illustrating a sample information obtaining apparatus (or analyzing apparatus) according to a fourth exemplary embodiment of the present invention.

FIG. 6 illustrates a fourth exemplary embodiment of the present invention. The present exemplary embodiment provides a method for detecting an electromagnetic wave. An apparatus of the present exemplary embodiment is similar in certain aspects to the analyzing apparatus of the second exemplary embodiment. Therefore, parts and features that are common to those of the second exemplary embodiment will not be described here.

FIG. 6 is a schematic diagram illustrating an analyzing apparatus of the present exemplary embodiment. As illustrated in FIG. 6, the analyzing apparatus of the present exemplary embodiment is obtained by adding a selection mechanism 501 to the analyzing apparatus of the second exemplary embodiment. Additionally, an electromagnetic wave detector 502 is provided downstream of the selection mechanism 501.

The functions and operation of the selection mechanism 501, electromagnetic wave detector 502, and processing unit 206 are the same as those according to the third exemplary embodiment.

Fifth Exemplary Embodiment

A fifth exemplary embodiment of the present invention will now be described. The present exemplary embodiment provides an analyzing apparatus which uses a linearly polarized wave as a terahertz wave. In the exemplary embodiments described above, the plane of polarization of a terahertz wave rotates relative to the polarization axis of the polarizer 102 in the testing device 100. However, in the present exemplary embodiment, a terahertz wave is incident on the sample 103 with its polarization angle kept constant with respect to the polarization axis of the polarizer 102.

For example, to set the angle of the polarization axis of the testing device 100 at 45 degrees with respect to the polarization direction of a terahertz wave, the rotation mechanism 301 or 401 described above is used to adjust this angle. Alternatively, to achieve a desired angle of the polarization axis of the testing device 100 with respect to the polarization direction of a terahertz wave, the positioning of the electromagnetic wave generator 201 and testing device 100 may be adjusted in advance. In this case, the rotation mechanism 301 or 401 used to adjust the angle is no longer needed.

The testing device 100 has the function of a polarizer. Therefore, the testing device 100 allows a terahertz wave to branch into an electromagnetic wave transmitted through the polarizer and an electromagnetic wave reflected off the polarizer, according to the angle of the polarization direction of the terahertz wave with respect to the polarization axis of the testing device 100. Then, these electromagnetic waves can be extracted as the orthogonal polarization component signal 204 and the parallel polarization component signal 205. By separately detecting these signals, transmittance measurement and reflectance measurement of the sample 103 are simultaneously performed. Also, by scanning the sample 103 with a terahertz wave incident thereon and plotting the measurement results, a transmitted image and a reflected image of the sample 103 can be simultaneously obtained. In other words, when signals of a transmitted electromagnetic wave and a reflected electromagnetic wave are individually determined with respect to each incident point at which an electromagnetic wave is incident on the sample 103, the resulting distributions of two-dimensional spatial arrangements of the signals can be obtained as a transmitted image and reflected image of the sample 103.

While the angle of the polarization axis of the testing device 100 with respect to the polarization direction of a terahertz wave is set at 45 degrees in the present exemplary embodiment, the angle is not limited to this value. The angle may be varied to compensate for variations in branching ratio caused by the presence of the sample 103. If the branching ratio is given in advance, the angle can be set at a predetermined value.

Sixth Exemplary Embodiment

A sixth exemplary embodiment of the present invention will now be described. The present exemplary embodiment provides a method for controlling the polarization of a terahertz wave. In the exemplary embodiments described above, a circularly polarized signal is obtained using the rotation mechanism 301 or 401. Therefore, the signal intensity of a detected terahertz wave continuously changes as shown in FIG. 8. In the present exemplary embodiment, the polarization direction is instantaneously changed without using such a circularly polarized signal, thereby performing operation similar to that described above.

More specifically, when a linearly polarized terahertz wave is used, the rotation mechanism 301 or 401 is used to allow sequential switching of the polarization direction of the terahertz wave between orthogonal and parallel directions relative to the polarization axis of the polarizer 102 in the testing device 100. According to this switching timing, the signal intensity of terahertz waves obtained from the testing device 100, that is, transmittance and reflectance intensity, is modulated in a square wave pattern as shown in FIG. 12. The processing unit 206 receives signals output from the electromagnetic wave detector 502 and processes a transmitted signal and a reflected signal separately, with reference to the switching timing described above.

With the configuration described above, transmittance measurement and reflectance measurement of the sample 103 are concurrently performed in the present exemplary embodiment. Additionally, by scanning the sample 103 with a terahertz wave incident thereon and plotting the measurement results, a transmitted image and a reflected image of the sample 103 can be substantially simultaneously obtained.

Seventh Exemplary Embodiment

A seventh exemplary embodiment of the present invention will now be described. The present exemplary embodiment provides a method for controlling the polarization of a terahertz wave. The polarization is mechanically controlled in the exemplary embodiments described above. However, in the present exemplary embodiment, the polarization is controlled by the configuration of an antenna for the electromagnetic wave generator 201.

To allow the signal intensity of a terahertz wave detected by a detector to continuously change as shown in FIG. 8, a spiral antenna is used as an antenna for the electromagnetic wave generator 201. Thus, since the polarization can be controlled by the antenna configuration, the rotation mechanism 301 or 401 of the above-described embodiments is no longer needed and the size of the apparatus can be reduced.

With the configuration according to any one of the exemplary embodiments described above, the present invention can improve accuracy of sample testing which involves the use of electromagnetic waves. Such an effect of the present invention is particularly significant when electromagnetic waves in the frequency range of 30 GHz to 30 Thz are used.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-125669 filed Apr. 28, 2006, which is hereby incorporated by reference herein in its entirety.

What is claimed is:
1. A sample information obtaining apparatus comprising:
an electromagnetic wave generator configured to generate electromagnetic waves;
a sample holding unit configured to provide a function of a polarizer having a polarization axis which defines how an incident electromagnetic wave is to be divided according to a polarization state of the incident electromagnetic wave, the sample holding unit being configured to hold a sample to be tested;

an electromagnetic wave detecting unit configured to separately detect a transmitted electromagnetic wave transmitted through the sample holding unit and a reflected electromagnetic wave reflected off the sample holding unit, the transmitted electromagnetic wave and the reflected electromagnetic wave being obtained by dividing the incident electromagnetic wave propagating from the electromagnetic wave generator and made incident on the sample holding unit, according to a relative positional relationship between the polarization state of the incident electromagnetic wave and the polarization axis of the sample holding unit; and a processor configured to process signals of the transmitted and reflected electromagnetic waves detected by the electromagnetic wave detecting unit and obtain information about the sample.

2. The sample information obtaining apparatus according to claim 1, wherein the sample information obtaining apparatus is configured such that the polarization state of the incident electromagnetic wave with respect to the polarization axis can be temporally varied.

3. The sample information obtaining apparatus according to claim 2, wherein at least one of the electromagnetic wave generator and the sample holding unit has a polarization state controller which temporally varies the polarization state of the incident electromagnetic wave with respect to the polarization axis.

4. The sample information obtaining apparatus according to claim 3, wherein the polarization state controller comprises a rotation mechanism for rotating the at least one of the electromagnetic wave generator and the sample holding unit.

5. The sample information obtaining apparatus according to claim 1, wherein the sample information obtaining apparatus is configured such that the polarization state of the incident electromagnetic wave with respect to the polarization axis can be fixed such that the incident electromagnetic wave has a component inclined with respect to the polarization axis.

6. The sample information obtaining apparatus according to claim 1, further comprising:
a scanning unit configured to vary a relative positional relationship between the sample held by the sample holding unit and the incident electromagnetic wave, in a direction in a plane of the sample facing an incident direction of the incident electromagnetic wave incident on the sample holding unit,
wherein the electromagnetic wave detecting unit detects the transmitted electromagnetic wave and the reflected electromagnetic wave at each electromagnetic wave incident point at which an electromagnetic wave is incident on the sample; and
a processor separately determines signals of the transmitted electromagnetic wave and reflected electromagnetic wave with respect to each electromagnetic wave incident point and obtains the resulting distributions of two-dimensional spatial arrangements of the determined signals as a transmitted image and a reflected image of the sample.

7. The sample information obtaining apparatus according to claim 1, wherein the electromagnetic wave detecting unit includes a plurality of detectors which detect the transmitted electromagnetic wave and the reflected electromagnetic wave separately from the sample holding unit.

8. The sample information obtaining apparatus according to claim 1, further comprising:
a selecting unit configured to sequentially select the transmitted electromagnetic wave and the reflected electromagnetic wave,
wherein one detector in the electromagnetic wave detecting unit detects the transmitted electromagnetic wave and the reflected electromagnetic wave.

9. The sample information obtaining apparatus according to claim 1, wherein the sample holding unit comprises a wire grid.

10. The sample information obtaining apparatus according to claim 9, wherein spaces between adjacent wires of the wire grid are filled with a filling material.

11. The sample information obtaining apparatus according to claim 9, wherein the sample is a solution that fills spaces between adjacent wires of the wire grid.

12. A sample information obtaining method comprising:
holding a sample to be tested on a sample holding unit configured to provide a function of a polarizer having a polarization axis which defines how an incident electromagnetic wave is to be divided according to a polarization state of the incident electromagnetic wave;
making an electromagnetic wave incident on the sample holding unit which holds the sample;
dividing the incident electromagnetic wave into a transmitted electromagnetic wave transmitted through the sample holding unit and a reflected electromagnetic wave reflected off the sample holding unit, according to a relative positional relationship between the polarization state of the incident electromagnetic wave and the polarization axis of the sample holding unit;
detecting the transmitted electromagnetic wave and the reflected electromagnetic wave separately; and
obtaining information about the sample on the basis of signals of the detected electromagnetic waves.

13. The sample information obtaining method according to claim 12, further comprising:
varying a relative positional relationship between the sample held by the sample holding unit and the incident electromagnetic wave, in a direction in a plane of the sample facing an incident direction of the incident electromagnetic wave incident on the sample holding unit;
detecting the transmitted electromagnetic wave and the reflected electromagnetic wave at each electromagnetic wave incident point at which an electromagnetic wave is incident on the sample;
separately determining signals of the transmitted electromagnetic wave and reflected electromagnetic wave with respect to each electromagnetic wave incident point; and
obtaining the resulting distributions of two-dimensional spatial arrangements of the determined signals as a transmitted image and a reflected image of the sample.

14. The sample information obtaining method according to claim 12, wherein the electromagnetic wave is a terahertz wave in the frequency range of 30 gigahertz to 30 terahertz.

15. The sample information obtaining method according to claim 12, wherein the polarization state of the incident electromagnetic wave with respect to the polarization axis is temporally varied.

16. The sample information obtaining method according to claim 12, wherein the polarization state of the incident electromagnetic wave with respect to the polarization axis is fixed such that the incident electromagnetic wave has a component inclined with respect to the polarization axis.

* * * * *